United States Patent [19]

Protasi et al.

[11] Patent Number: 5,066,786
[45] Date of Patent: Nov. 19, 1991

[54] METHOD FOR THE PURIFICATION OF INTERFERON

[75] Inventors: Otello Protasi; Paolo Rappuoli, both of Siena, Italy

[73] Assignee: Sclavo, S.p.A., Siena, Italy

[21] Appl. No.: 220,312

[22] Filed: Jul. 18, 1988

[30] Foreign Application Priority Data

Jul. 31, 1987 [IT] Italy .................. 21560 A/87

[51] Int. Cl.$^5$ .................. C07K 15/26; C07K 3/18; C07K 3/20
[52] U.S. Cl. .................. 530/351; 530/415; 530/417; 435/69.51
[58] Field of Search .................. 530/351, 415, 417; 435/69.51

[56] References Cited

U.S. PATENT DOCUMENTS

| | | | |
|---|---|---|---|
| 3,897,309 | 7/1975 | Grabner | 435/229 |
| 4,168,261 | 9/1979 | Edy | 530/351 |
| 4,485,017 | 11/1984 | Tan et al. | 210/635 |
| 4,485,038 | 11/1984 | Chadha et al. | 530/351 |
| 4,617,378 | 10/1986 | Rubinstein et al. | 530/351 |
| 4,894,330 | 1/1990 | Hershenson et al. | 435/69.51 |

OTHER PUBLICATIONS

Tan, Y. H., 1981, Methods in Enzymology 78:422–430.

*Primary Examiner*—Margaret Moskowitz
*Assistant Examiner*—Keith C. Furman
*Attorney, Agent, or Firm*—Hedman, Gibson, Costigan & Hoare

[57] ABSTRACT

A method is described for the purification of crude human interferon from solutions containing it, which comprises:

a) the complete adsorption of the crude interferon in a column of siliceous material which has previously been disinfected with an aqueous solution of formaldehyde;

b) the washing of the column with non-pyrogenic, sterile, deionized water;

c) the removal of the extraneous residual proteins by the elution of the column successively with a 1.4 M aqueous solution of NaCl in non-pyrogenic, sterile, deionized water, and with an aqueous solution of acetic acid having a molar concentration of 0.001 M to 0.003 M;

d) the elution of the interferon from the column with an aqueous solution of acetic acid having a molar concentration of from 0.01 to 0.03 M and finally, e) the recovery and lyophilization of the elution containing the purified interferon.

The method enables interferon to be obtained, the purity of which, measured as its specific activity, is at least 1000 times greater than that of the crude interferon, with a yield greater than 85%.

The interferon thus purified is particularly useful for treatment in man.

12 Claims, 4 Drawing Sheets

METHOD FOR THE PURIFICATION OF INTERFERON

The present invention relates to a method for the purification of interferon.

The present invention particularly concerns an improved method for the purification of human interferon (hu-IFN) from solutions which contain it.

Interferons are glycoproteinaceous substances with high molecular weights, and hydrophobic properties, generally being divided into alpha, beta and gamma interferons.

The glycoproteins are synthesized by human and animal cells in response to viral and non-viral agents during the first stages of an infection and represent one of the main defense mechanisms of an organism.

In particular, alpha and beta interferons are produced by the leucocytes and by the fibroblasts respectively and have a predominantly antiviral activity, while gamma interferon demonstrates a mainly neoplastic immunoregulation and immunosurveillance activity.

Interferons are particularly useful as antiviral agents, since they are non-toxic, natural substances which can confer effective protection against numerous pathogenic agents.

The substances, and in particular beta-IFN, can also be used as adjuvants in secondary immunodeficiency to viral infections and in the oncological sector.

The use of these substances for treatment in man requires the availability of interferon which has a high degree of purity, measured as the specific activity, of no less than $1 \times 10^6$ International Units (I.U.) /mg of protein, which can easily be lyophilized, and is very stable.

Numerous methods are known in the art for the purification of interferon by means of chemico-physical treatments [Knight et al. J of Biol. Chem. 250, 4139 (1975)], or by means of chromatographic treatments which use particular adsorbent materials or particular elution solvents.

For example U.S. Pat. No. 3 414 651 describes a method for the purification of interferon from solutions containing contaminating substances, which comprises the adsorption of the solution in a column of Neosyl or Aerosil, the elution of the column with a pH 5.0 solution of an iodic or thyocyanate salt, the precipitation of the contaminating proteins present in the eluate at a pH less than 5.0, and the precipitation of the interferon by means of an organic solvent such as methanol or acetone. The interferon thus precipitated is dissolved again in water (pH 7.5) and the solution is purified on an anionic resin.

U.S. Pat. No. 4 485 017 describes a method for the purification of interferon by means of affinity chromatography and subsequent high-pressure chromatography.

Patent No. EP 11435 describes and claims a method for the purification of a solution of beta-interferon by means of chromatophraphy on a cationic resin and subsequent chromatography of the eluate on a carrier containing $Ni^{++}$, $Co^{++}$, $Zn^{++}$ or $Cu^{++}$ ion-chelating groups which can bind the interferon.

These methods, however, are complicated due to the many operations required, the use of numerous reagents, and the generally mediocre yields, which make the methods uneconomical and therefore not very suitable for use on a commercial scale.

Other methods have therefore been proposed in the art for the purification of interferons, based essentially on the use of a porous glass material which can bind the interferon hydrophobically (Lampson et al. 1963 Proc. Soc. Exper. Biol. and Med. 112, 468,478; Davies et al, 1965 Biochem. J. 95, 251–255).

In particular U.S. Pat. No. 4,168,261 describes a method for the purification of a solution of interferon which comprises placing the solution in contact with a buffered saline solution, eluting the residual contaminating material with a 0.01 M glycine-HCl mixture (pH 2.5) and finally removing the interferon bound to the material by eluting it with a 0.1 M KCl-HCl mixture (pH 2.0).

When this method is used, however, there is, on the one hand partial purification of the interferon and on the other hand a low production yield.

The method consequently has little attraction and is of no great interest for commercial use.

In fact it has been found that the method described above is greatly affected both by the elution solvents selected and by the conditions under which steps of the adsorption and the elution of the interferon are conducted.

There is ample literature in this connection, in which methods are described for the purification of interferon adsorbed on a glass material, particularly on CPG, based on the use of certain elution solvents or particular operative conditions.

In this connection U.S. Pat. No. 4,485,038 and the work of H. TAN, Methods in Enzymology Vol. 78, page 424 (1981) are cited.

The U.S. patent '038 describes and claims a method for the purification of alpha interferon from solutions which contain it by means of adsorption on CPG.

A fundamental characteristic is the fact that the interferon is eluted by means of a mixture of polyethylene glycol (4.1 M) and NaCl (1M) at a pH no less than 4.1.

By means of the above-described operation, a high yield of alpha-interferon is obtained but its purity is such as to make a further treatment of the alpha-IFN necessary, by means of chromatography on cationic resin and on phenyl agarose.

H.TAN describes a method for the purification of beta-interferon, partially purified on CPG, by means of subsequent chromatography on CM-cellulose and SDS-PAGE.

This method, however, is not completely satisfactory, particularly in view of the numerous stages required, the low production yields and the difficult of lyophilizing the fractions of interferon thus obtained.

The subject of the present invention is therefore a method for the purification of interferon without, or substantially without, the problems described above.

Another subject of the present invention is the use of interferon thus purified for treatment in man.

Further subjects of the present invention are pharmaceutical compositions containing a quantity of interferon thus purified, which is therapeutically effective in mammals, including man.

Further subjects of the present invention will become clear from a reading of the following description and examples.

The present invention is based essentially on the fact that the purification of interferon, with the use of non-buffering washing solutions and eluent solutions containing low molar concentrations of a solvent with hydrophobic and acidic properties, is effected in a single chromatographic step with yields greater than 85%, obtaining interferon whose purity is increased at least 1000 times in comparison with the IFN loaded, and which is stable and can easily be lyophilizing.

Accordingly, the present invention relates to a method for the purification of human interferon from a solution containing it, which comprises:

a) the complete adsorption of the crude interferon contained in the solution to be purified in a column of siliceous material which has previously been disinfected with an aqueous solution of formaldehyde;

b) the washing of the column with non-pyrongenic, sterile, deionized water;

c) the removal of the residual extraneous proteins by the elution of the column successively with a 1.4 M aqueous solution of NaCl, in a non-pyrogenic sterile deionized water, and an aqueous solution of a solvent with hydrophobic and acidic properties at a molar concentration of from 0.001 M to 0.003 M;

d) the elution of the interferon from the column with an aqueous solution of the same solvent as that used in step c) at a molar concentration of from 0.01 to 0.03 M, and finally, e) the recovery and lyophilization of the elution containing the interferon thus purified.

According to the present invention, the crude interferon solution may be a biological liquid or an aqueous solution obtained by the culture of human cells.

Preferably a beta-interferon solution obtained from human fibroblasts cultured according to one of the methods known in the art, is used.

In particular, human diploid fibroblasts may be grown in a submerged culture by the microcarrier technique in a Dulbecco medium (DMEM) in the presence of interferon inductors at a temperature of about 30° C.

In step a) of the method according to the present invention, the crude interferon is adsorbed in a column of siliceous material by the loading of the solution at a spatial velocity (rate of flow/volume of adsorbent material) of from 0 to $40 \times h^{-1}$ by means of an automatic system provided with a peristaltic pump.

The loading is conducted at atmospheric pressure and at a temperature of about 4° C.

Chromatographic columns suitable for the purpose may be of various sections and lengths and are selected from those available commercially.

During the loading stage, the interferon is bound hydrophobically to the siliceous material, while most of the extraneous proteins remain in solution and are discharged from the column.

The pH during the contact stage between IFN and the adsorbent material is that of the solution supplied.

According to the method of the present invention, suitable siliceous materials for the purpose are selected from those which can bind the interferon hydrophobically and which are available commercially under various trade marks. Preferably controlled-porosity glass materials (CPG) are used.

Among these, CPG 10-350(Electro Nucleonics Inc.) is particularly preferred, its characteristics being: Mesh size 120/200, average pore diameter 350 Angstrom (Å), pore spacing 6.5 (±%), pore volume 0.91 (cc/g), surface area 53.45 (m²/g).

The quantity of siliceous material used for the preparation of the column is determined so as to obtain the highest possible binding ratio of interferon loaded/ml of adsorbent material.

In fact this enables the complete adsorption of the interferon loaded, the production of a compact peak which corresponds to purified IFN, and the preparation of the fractions with a high pure interferon content. According to the present invention, it has been found that when operating under the preferred conditions, the binding ratio is between $0.3 \times 10^7$ and $1.2 \times 10^7$ I U. of "eta-IFN/ml of CPG 10-350."

The determination of this ratio can, in any case, easily be established by an expert in the art.

After the column has been packed with the adsorbent material, it is disinfected with an aqueous solution of formaldehyde.

In practice the column is left in static contact with a 10% (V/V) aqueous formaldehyde solution at ambient temperature (20°-25° C.) for 1 night.

The column is then washed with non-pyrogenic sterile deionized water (neutral pH) until the formaldehyde has been completely removed and the crude interferon solution to be purified is then loaded.

Upon completion of the loading stage, the column is washed with non-pyrogenic, sterile, deionized water until the effluent is zeroed at 280 nm. The use of deionized water has been found to be particularly advantageous for the purification method according to the present invention.

In fact it has been found that the buffer solutions which are generally used in known techniques, cause the elution of interferon to be slowed down when acid eluent solutions at low molar concentrations are used. This is probably due to the fact that the column remains buffered and the pH conditions necessary for the removal of the IFN from the adsorbent material with a fairly low-molarity eluent solution are reached more slowly. In step c) of the method according to the present invention, the residual extraneous proteins are removed by the elution of the column successively with a 1.4 M aqueous NaCl solution, with non-pyrogenic, sterile, deionized water and finally with an aqueous solution of a solvent having hydrophobic and acidic properties, at a molar concentration of from 0.001 M to 0.003 M.

According to the present invention, the solvent used is preferably acetic acid and its concentration is preferably 0.002 M (pH 3.7).

The analysis of the individual eluents, effected by means of the determination of the biological activity of IFN according to Armstrong J.A. (1981), Methods Enzymol 78,381-387, does not reveal the presence of interferon, thus indicating stable binding of the interferon loaded with the adsorbent material.

In stage e), the method according to the present invention then proceeds with the removal of the interferon from the adsorbent material by elution with an aqueous solution of acetic acid at a molar concentration of from 0.01 M to 0.03 M, preferably 0.024 M (pH 3.2) and the recovery of the fraction which corresponds to the interferon peak.

Alternatively fractions with a different IFN content may be collected separately in correspondence with the ascending and descending phases of the IFN peak.

The beta-interferon yield from the operation described above, calculated as the total of beta-IFN units eluted in comparison with the total loaded, is between 60–70% and the beta-IFN specific activity is increased at least 1000 times.

According to another version of the method according to the present invention and in order to increase the beta-IFN production yield, the column is left in static contact with the aqueous acetic acid solution (0.01 M–0.03 M) for a period of from 15 to 30 minutes, after the elution has been carried out as described in step d), and then, after the peristaltic pump has been restarted, another fraction of beta-IFN is eluted. This operation is repeated until the absorbance of the eluate at 280 nm is approximately 0.05 AFSU (Arbitrary Full Scale Units). Arbitrary Full Scale consists of a scale established experimentally by the researchers and are between the given values 0 and 100 on the registration paper connected with the flux cell used for performing the absorbance measure. The 0 corresponds to the absorbance of the pure solvent white 100 corresponds to the maximal value of absorbance registered during the experiment.

With the procedure described above an overall beta-INF yield greater than 85% is obtained.

Upon completion of the elution stage, the column is treated with a 5 M aqueous solution of acetic acid, suitably washed, and then reused for a subsequent purification.

Beta-IFN fractions thus purified and kept at a temperature of 4° C. do not show a significant change in biological activity after 6–12 months.

The fractions may be used as they are or may be lyophilized by one of the generally-known techniques.

In particular a lyophilization cycle is used which is established to take into account the thermolability factor of the beta-IFN molecule and which falls within the scope of the present invention.

In practice, HSA and mannitol are added to the beta-IFN fractions and they are then filtered, under sterile conditions, through a DURAPORE (Millipore) a difluoropolyvin membrane having a pore diameter of 0.22 $\mu$m (Millipore), which has previously been treated with a 0.024 M aqueous solution of acetic acid containing 2 mg/ml of HSA at ambient temperature (20°–25° C.) for approximately 1 hour and then washed with a 0.024 M aqueous acetic acid solution.

The filtered beta-IFN fractions are collected in a sterile container and then introduced into sterile-non-pyrogenic glass bottles.

According to the present invention, the bottles containing the beta-IFN solutions are then placed in direct contact with the lyophilization freezer plate at a temperature of approximately $-42°$ C.

Subsequently, in the first lyophilization stage, the plates are brought to a temperature of approximately $+8°$ C. and kept at that temperature for 9 hours.

The product within the bottles reaches a temperature of $-20°$ C.

The plates are then brought at a constant gradient from $+8°$ C. to $+26°$ C. in approximately 15 hours. During this stage the product reaches a temperature of $+20°$ C.

In the second lyophilization stage, the temperature of the plates is kept at $+26°$ C. for approximately 24 hours and the temperature of the produce reaches a value of approximately $+22°$ C.

Finally, in order further to dry the product and achieve a residual humidity less than 2%, the temperature of the plates is brought to a value of approximately $+28°$ C.

After a period of approximately 8 hours it is observed that the plate and the product have a uniform temperature of 24° C.

The drying is continued for a further 1 hour and the bottles are then closed in an atmosphere of nitrogen, which has previously been dehydrated on silica gel and filtered.

By means of the operation described above, a lyophilate yield of more than 75% is obtained, calculated in comparison with the crude beta-IFN, the lyophilate being white in colour and easily soluble in its diluent, to produce a solution having a pH of 4.5 or approximately 4.5, and having a residual humidity no greater than 2%.

Stability tests carried out on the product in the lyophilized state and after reconstitution, do not show any significant loss in biological activity. Moreover, having undergone sterility tests, the product appears to be free of bacteria and fungi and does not contain endotoxins or pyrogens.

The beta-interferon thus purified may be used for the preparation of pharmaceutical compositions useful for treatment in man.

In particular these compositions may be formulated in the form of creams or gels for topical application, sterile solutions for parenteral injection, nasal sprays, and liquids for ocular instillation, or collutories.

The quantity of lyophilized interferon used in these compositions is selected on the basis of the effect desired, the particular formulation, the duration of the treatment and the daily dose.

The beta-interferon is generally formulated together with excipients such as human albumin and mannitol and stabilizers selected from those known in the art.

According to the present invention, injectable compositions, creams and liquids for ocular instillation have been used in patients affected by the following conditions of viral etiology:

a) opthalmology: herpetic keratitis and kerato-conjunctivitis by adenovirus;

b) dermatology, gynaecology and urology:
   infections of the dermis or of the mucous membranes by Herpes Simplex types 1 and 2;
   lesions of papilloma virus (HPV)

c) localized or generalized infections by herpes zoster.

The clinical results obtained with the use of beta-interferon produced in accordance with the present invention lead to the following observations: in general, beta-interferon is shown to be at least as effective as the antiviral chemotherapeutic agents used as comparisons, having a better tolerability and selectivity of action against the infected cells than the latter; a further advantage, both in topical and in systemic treatment, is that resistance to the treatment is not induced and in the event of recurrence the therapeutic power of the drug therefore remains unimpaired, it may also be useful to take advantage of the synergistic action of beta-interferon and antiviral chemotherapeutic agents, so that the incidence of any side effects of the latter may be reduced by the reduction of the doses thereof.

Elution of beta-interferon with 0.024 M acetic acid, where:

s = the loading of crude beta-IFN

Figure 1:
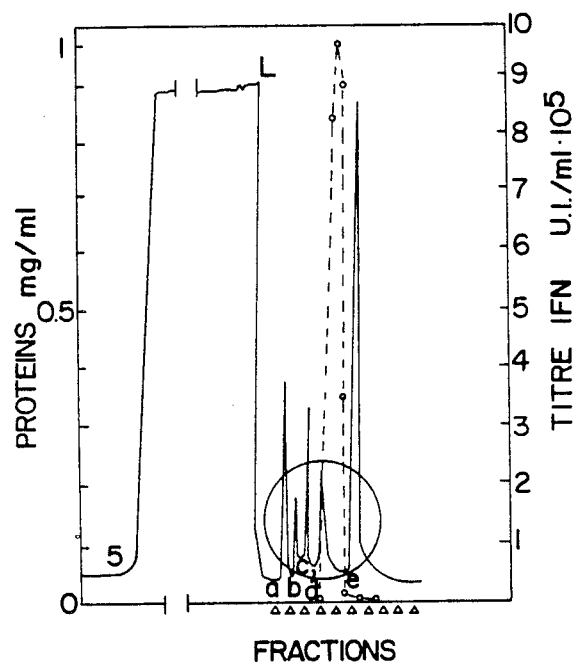
FIG. 1–1A
Figure 1A:
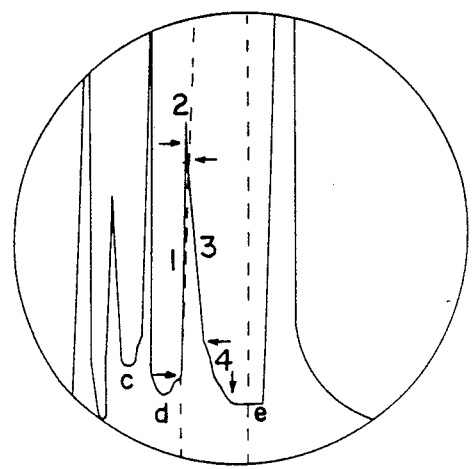

L = the washing of the column with non-pyrogenic, sterile, deionized water a = the treatment of the column with 1.4 M NaCl b = the washing with non-pyrogenic, sterile, deionized water c = the treatment with 0.002 M acetic acid d = the elution of beta-INF with 0.024 M acetic acid e = the treatment of the column with 5 M acetic acid
_____ = protein concentration
----- = biological activity FIG. 1A is a portion of FIG. 1 that has been enlarged for clarity.

FIG. 2

Figure 3:
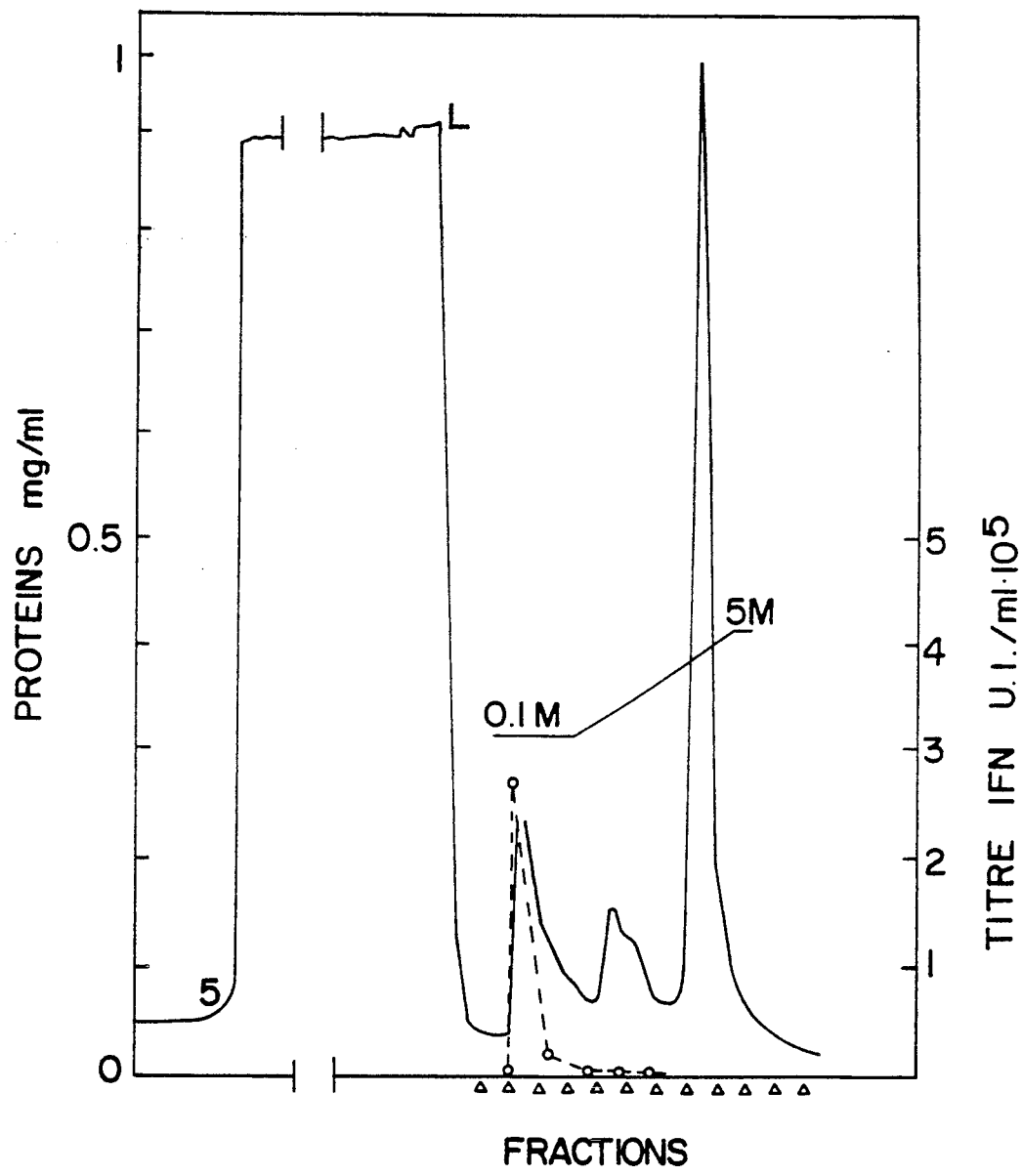

The elution of beta-IFN with 0.024 M acetic acid, where: a, b, c, and d have the same meaning as in FIG. 1;

_____ = protein concentration
----- = biological activity FIG. 3

The elution of beta-INF with 0.1 M acetic acid in 0.15 M NaCl+0.2 g/l HSA
s = the loading of crude beta-IFN
L = the washing of the column with 0.2 g/l PBSA+HSA
_____ = protein concentration
----- = biological activity

FIG. 4 shows the cycle for the lyophilization of purified beta-IFN
_ _ = the pressure in the lyophilization chamber
_ _ = programmed temperature of the plates
_ _ = effective temperature of the plates
----- = effective temperature of the plates
_____ = temperature of the product
● ● ● = temperature of the condenser.

The following experimental examples are illustrative and not limiting of the invention itself.

EXAMPLE 1

The preparation of human beta-interferon

Diploid fibroblasts obtained from the foreskins of newborn infants CSC 506 (Flow Laboratories, Inc. Mc.Lean, Virginia) are grown in submerged cultures by the microcarrier technique, in two bioreactors each with a capacity of 50 l, containing 35 l of Earle's medium modified by Bulbecco (DMEM) with the addition of 5% foetal bovine serum (FBS) at 30° C. for 48 hours.

At the end of this period, the culture is washed twice with EARLE's solution and DMEM is then added, containing 0.1% of human albumin and 50-100 I.U. of human beta-IFN.

After 15 hours, the culture medium is removed and replaced by DMEM medium containing 50 µg/ml of Poli I Poli C (P-L Biochemicals Inc. Milwaukee, USA) and 10 µg/ml of cycloheximide (Sigma Chemical Co., St. Louis USA) and after 4 hours 1 µg/ml of Actinomycin D- is added.

The culture is again washed with EARLE's solution and DMEM is added containing 0.025% of human albumin.

After 36 hours at 30° C., the culture medium is separated from the microcarriers and collected directly in sterile stainless steel containers kept at a temperature of 4° C.

The solution is then filtered through Sartorius Sartopure cartridges (1.2 µm) so as to separate the cells, and the filtrate is recovered and kept at 4° C.

EXAMPLE 2

The purification of beta-interferon a) Preparation of the chromatography column A column K 100 mm×45 cm (Pharmacia) is packed with 165 ml of controlled-porosity glass material CPG 10-350 (Electro Nucleonics Inc.) and then disinfected by being left in static contact with an aqueous solution of formaldehyde (10% V/V) at ambient temperature (10° C.-25° C.) for 1 night.

The column is then washed with 50 l of non-pyrogenic sterile deionized water until complete removal of the formaldehyde has been achieved, determined according to the method of Critchfield, F.E. et al. (1957) Anal. Chem. 29, 797, and brought to a temperature of 4° C. The solution containing crude beta-interferon prepared as described in Example 1 is then supplied continuously by means of an automatic system including a Masterflex-model peristaltic pump.

b) Purification of beta-interferon 100 l of crude beta-interferon solution from three different fermentations having an average total protein content of 0.92 mg/ml with $1.9 \times 10^4$ international units (I.U.) /mg of protein (specific activity) and $1.75 \times 10^4$ I.U. /ml of crude beta-interferon (biological activity) are loaded into the column of CPG 10-350 at a rate of 5 l/hour.

It is found that when operating in this manner the CPG retains $1.1 \times 10^7$ I.U. of beta-IFN/ml of "CPG 10-350."

The column is then washed with approximately 20 liters of non-pyrogenic, sterile, deionized water, supplied at a rate of 5-6 l/hour, until the absorbance of the effluent is zero, measured at 280 nm using an optical unit (Pharmacia) model UV-1 with an industrial flow cell having a 1 cm optical path.

The residual extraneous proteins are then removed from the column by the supply in succession at a rate of 2 l/hour of 1.5 l of a 1.4 M aqueous solution of NaCl (9 column volumes C.V.), 2 l of non-pyrogenic, sterile, deionized water (12 C.V.) and 2 l of a 0.002 M aqueous solution of acetic acid (ANALAR BDH) (pH 3.7) (12 C.V.).

The testing of the eluates, effected according to I.A. Armstrong's method (1981) Methods Enzymol. 78, 381-387 does not reveal the presence of beta-interferon biological activity.

Finally, the CPG 10-350 column is eluted with approximately 1.085 l (6.5 C.V.) of a 0.024 M aqueous solution of acetic acid (pH 3.2) supplied at a rate of 2 l/hour and 4 fractions are collected of the peak which corresponds to beta-IFN (FIG. 1, peak d). Table I below gives the volumes and specific and biological activities of beta-IFN for the 4 fractions thus separated.

TABLE I

|  | Vol. | C.V. | IFN beta | Tot. Prot. | Specific Act. |
| --- | --- | --- | --- | --- | --- |
| Fr. No. 1 | 50 ml | 0.3 | 837,000 IU/ml | 0.06 mg/ml | $1.39.10^7$ IU/mg |
| Fr. No. 2 | 95 ml | 0.6 | 2,438,000 IU/ml | 0.20 mg/ml | $1.22.10^7$ IU/mg |
| Fr. No. 3 | 455 ml | 2.7 | 1,173,000 IU/ml | 0.10 mg/ml | $1.17.10^7$ IU/mg |
| Fr. No. 4 | 485 ml | 3 | 368,000 IU/ml | 0.05 mg/ml | $0.74.10^7$ IU/mg |

After this elution, the pump is stopped and the column is left in static contact with the 0.024 M acetic acid solution for approximately 15 minutes, the pump is then restarted (at a rate of 2 l/hour) and another fraction is collected.

This operation is repeated 8 times, the static contact time being increased up to a maximum of 30 minutes.

The fractions collected have the following characteristics:

|            | Vol.   | C.V. | IFN B           | Tot. Prot.  | Specific Act.     |
|------------|--------|------|-----------------|-------------|-------------------|
| Fr. No. 5  | 180 ml | 1.1  | 1,063,000 IU/ml | 0.10 mg/ml  | $1.06.10^7$ IU/mg |
| Fr. No. 6  | 180 ml | 1.1  | 455,000 IU/ml   | 0.08 mg/ml  | $0.57.10^7$ IU/mg |
| Fr. No. 7  | 130 ml | 0.8  | 451,000 IU/ml   | 0.08 mg/ml  | $0.56.10^7$ IU/mg |
| Fr. No. 8  | 150 ml | 0.9  | 253,000 IU/ml   | 0.06 mg/ml  | $0.42.10^7$ IU/mg |
| Fr. No. 9  | 150 ml | 0.9  | 874,000 IU/ml   | 0.17 mg/ml  | $0.51.10^7$ IU/mg |
| Fr. No. 10 | 115 ml | 0.7  | 169,000 IU/ml   | 0.04 mg/ml  | $0.42.10^7$ IU/mg |
| Fr. No. 11 | 140 ml | 0.8  | 127,000 IU/ml   | 0.02 mg/ml  | $0.63.10^7$ IU/mg |
| Fr. No. 12 | 150 ml | 0.9  | 127,000 IU/ml   | 0.01 mg/ml  | $1.27.10^7$ IU/mg |

Considering only the peak d of the chromatogram (FIG. 1), the purification yield (beta-IFN eluted/beta-IFN supplied), is approximately 60% whilst the yield including the further 8 fractions is approximately 88%.

The specific activity of the beta-IFN is increased approximately 730 times in comparison with the crude beta-IFN.

EXAMPLE 3

Purification of beta-interferon 70 l of a solution of crude beta-interferon having a total protein content of 0.92 mg/ml with a specific activity of $1.9 \times 10^4$ I.U. beta-IFN/mg of protein and a biological activity of $1.35 \times 10^9$ I.U. of beta-IFN are loaded at a rate of 5 l/hour into a column K 100 mm×45 cm (Pharmacia) packed with 280 ml of "CPG 10-350" and disinfected as described in example 2 above.

The binding ratio found is $4.82 \times 10^6$ IU of beta-IFN/ml of CPG 10-350.

Figure 2:
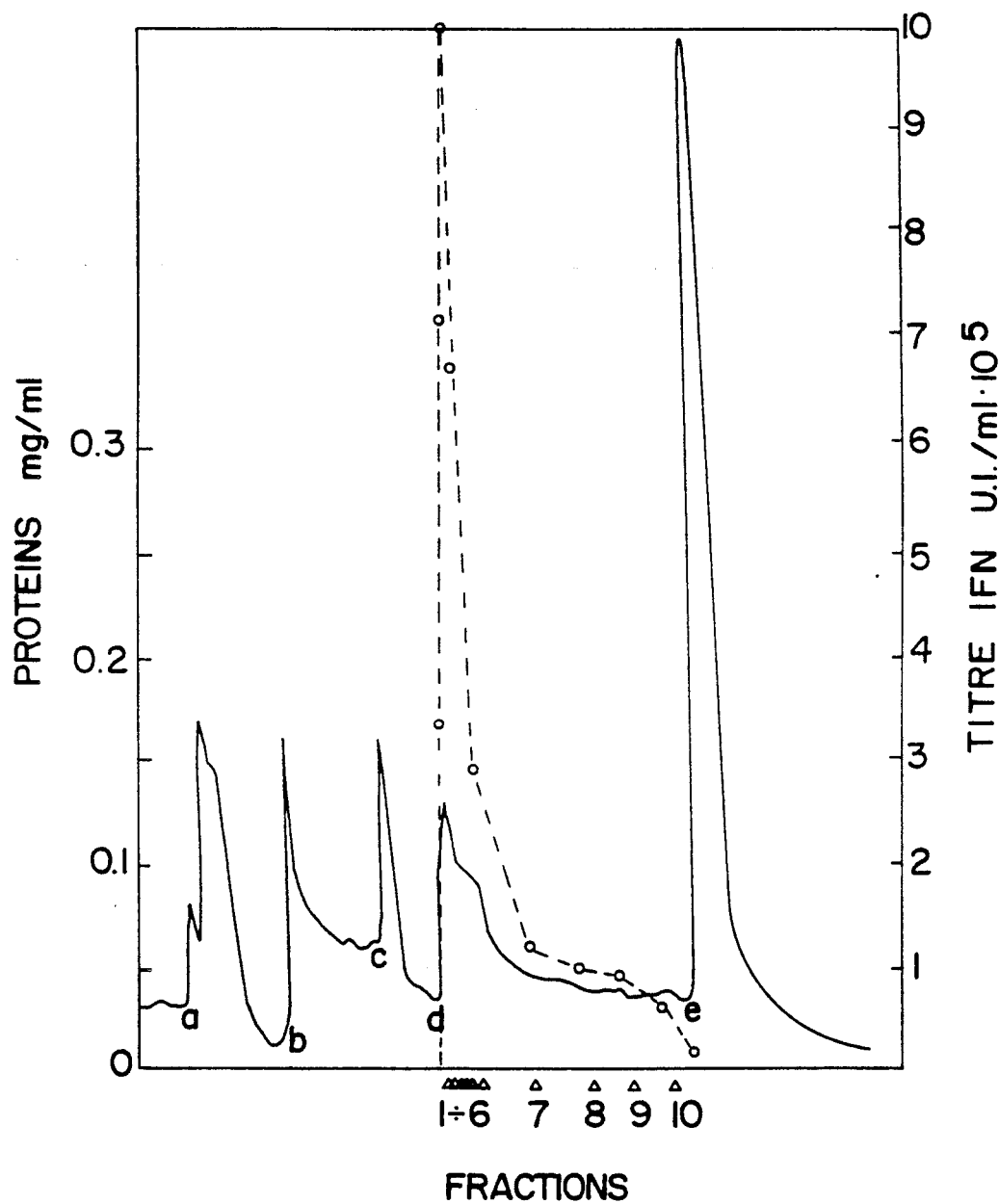

After the column has been washed and the residual extraneous proteins removed as described in Example 2, the beta-interferon is eluted from the column with approximately 3.6 l (12.7 c.v.) of an 0.024 M aqueous solution of acetic acid (pH 3.2) and 10 fractions of the peak d (FIG. 2) are collected.

Table II gives the volumes and beta-IFN biological activities, the protein totals and the specific activities for the 10 fractions.

| FRACTION | VOLUME | C.V. | beta-IFN        | TOT. PROT   | SPEC. ACT        |
|----------|--------|------|-----------------|-------------|------------------|
| No. 1    | 200 ml | 0.3  | 356,000 IU/ml   | 0.080 mg/ml | $0.44.10^7$ IU/mg |
| No. 2    | 150 ml | 0.5  | 729,000 IU/ml   | 0.100 mg/ml | $0.73.10^7$ IU/mg |
| No. 3    | 200 ml | 0.7  | 1,170,000 IU/ml | 0.150 mg/ml | $0.78.10^7$ IU/mg |
| No. 4    | 400 ml | 1.4  | 655,200 IU/ml   | 0.100 mg/ml | $0.65.10^7$ IU/mg |
| No. 5    | 500 ml | 1.8  | 287,200 IU/ml   | 0.015 mg/ml | $1.91.10^7$ IU/mg |
| No. 6    | 460 ml | 1.6  | 125,000 IU/ml   | 0.008 mg/ml | $1.56.10^7$ IU/mg |
| No. 7    | 410 ml | 1.5  | 100,000 IU/ml   | 0.008 mg/ml | $1.25.10^7$ IU/mg |
| No. 8    | 500 ml | 1.8  | 98,000 IU/ml    | 0.008 mg/ml | $1.22.10^7$ IU/mg |
| No. 9    | 470 ml | 1.7  | 66,000 IU/ml    | 0.007 mg/ml | $0.94.10^7$ IU/mg |
| No. 10   | 470 ml | 1.7  | 7,800 IU/ml     | 0.007 mg/ml | $0.11.10^7$ IU/mg |

The purification yield is 68% with the specific activity of beta-IFN being increased 1000 times in comparison with crude beta-IFN.

EXAMPLE 4

Comparison

The purification of the crude beta-interferon solution is carried out as described in Example 2 above, using a physiological buffered solution (PBSA) pH 7.2, containing 0.2 g/l of human albumin (HSA) for the washing of the "CPG 10-350" column, and eluting the beta-IFN with a 0.1 M aqueous solution of acetic acid (pH 2.9) as described in the prior art (Tan H. Methods in Enzymology Vol. 78, 424, 1981).

In practice, after the loading of the solution to be purified and the washing of the column with the buffered solution, the treatment of the CPG is effected with 0.1 M acetic acid in 0.15 M NaCl containing 0.2 g/l of HSA.

FIG. 3 shows the chromatogram relating to this elution.

The yield obtained is 50% with an average specific activity of the fractions of $0.5 \times 10^6$ I.U./mg.

These fractions are difficult to lyophilize, mainly because of their excessive acidity (pH 2.9).

Under these conditions, in fact, in addition to the beta-IFN, a large quantity of extraneous proteins is eluted with an isolectric point at a pH of about 4.0–4.5.

Thus subsequent lyophilization, which involves an increase in pH, causes their precipitation with consequent opalesence and loss of biological activity in the lyophile after its reconstitution in water.

EXAMPLE 5

Figure 4:
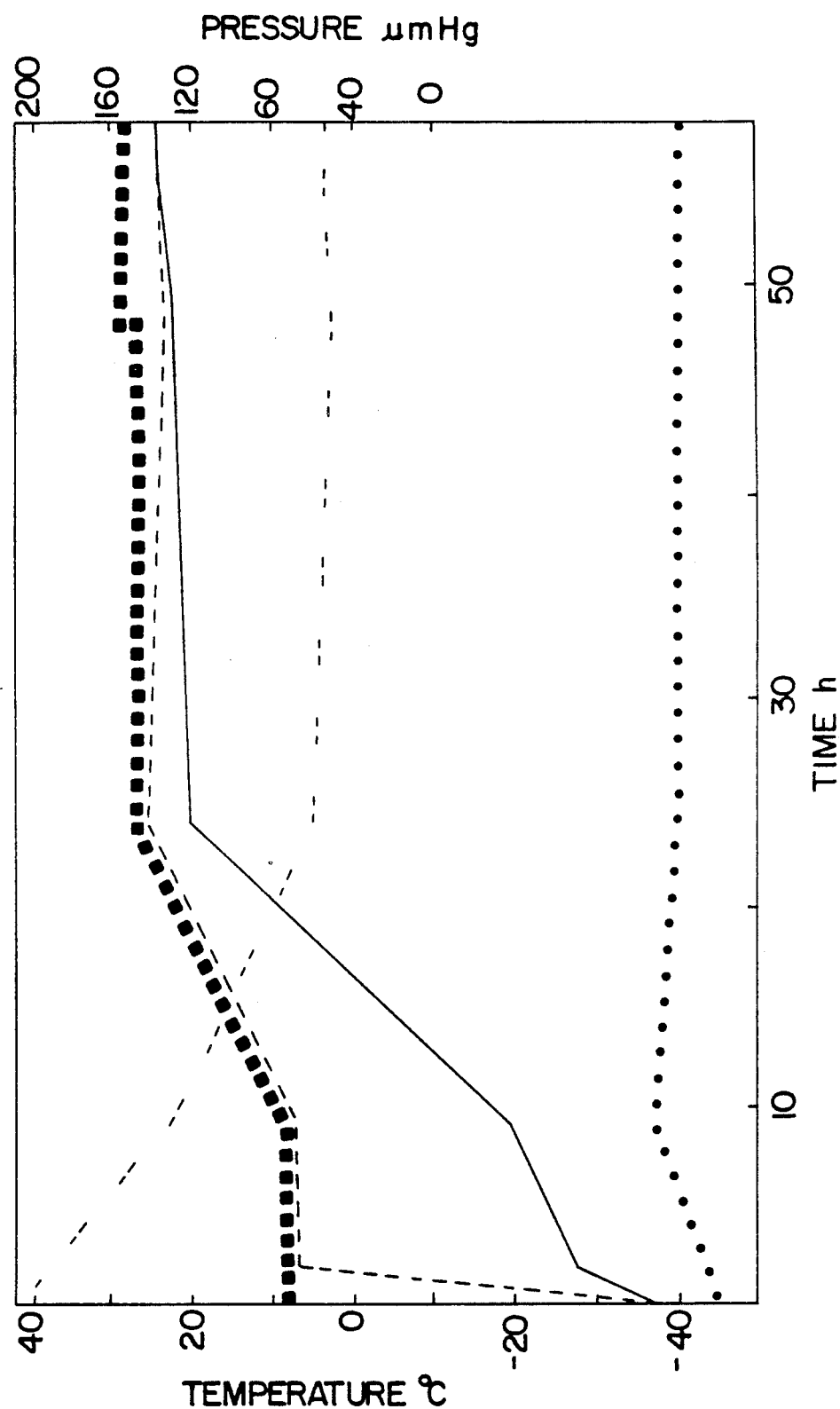

Lyophilization of Purified Beta-IFN (FIG. 4)

HSA (2mg/ $1.10^6$ I.U. of beta-IFN), mannitol (40 mg/$1.10^6$ I.U of beta-IFN) are added to the beta-IFN fractions and filtered under sterile conditions through a 0.22 μm Durapore membrane (Millipore) which has previously been treated with an 0.024 M aqueous solution of acetic acid containing 2 mg/ml of HSA, at ambient temperature (20°–25° C.), for approximately 1 hour and then washed with an 0.024 M aqueous solution of $CH_3COOH$.

The filtered beta-IFN fractions are collected in sterile containers and then introduced into sterile non-pyrogenic glass bottles by means of Farmatic semi-automatic or automatic machines provided with Class 100 vertical laminar air-flow hoods.

The bottles containing the pure beta-IFN solutions are placed in direct contact with the freezing plate of the lyophilizer (Edwards Minifast 1700) at a temperature of approximately −42° C. Subsequently, in the first lyophilization stage, the plates are brought to a temperature of approximately +8° C. and kept at that temperature for 9 hours. The product within the bottles reaches a temperature of −20° C.

The plates are then brought at a constant gradient, from +8° C. to +26° C. in approximately 15 hours. During this stage the product reaches a temperature of +20° C.

The temperature of the plates is kept at +26° C. for approximately 24 hours and the temperature of the product reaches a value of approximately +22° C.

Finally, in order further to dry the product and to achieve a residual humidity less than 2%, the temperature of the plates is brought to a value of approximately +28° C.

After a period of approximately 8 hours it is observed that the plates and the product have a uniform temperature of +24° C.

Drying is continued for a further 1 hour and the bottles are then closed in an atmosphere of nitrogen, which has previously been dehydrated on silica gel and filtered through "ACRO-50", (Gelman) a hydrophobic filter, having a pore diameter of 0.45 μm.

The average ratio between the lyophilized beta-IFN and the crude beta-IFN is 76%.

The stability test carried out on the lyophile as such and after reconstitution in water, by the accelerated method, gives the following results:

LYOPHILE STABILITY TEST
Accelerated Method
(Retention of antiviral activity)

| Time | % Antiviral Activity | | | | |
|---|---|---|---|---|---|
| | +4° C. | +25° C. | +31° C. | +37° C. | +45° C. |
| days 0 | 100 | 100 | 100 | 100 | 100 |
| days 1 | — | — | — | 92 | 98 |
| days 2 | — | — | 100 | 96 | 73 |
| days 3 | — | — | — | 93 | 69 |
| days 4 | — | — | — | 90 | 60 |
| days 5 | — | — | — | — | — |
| days 6 | — | — | — | — | — |
| days 7 | — | — | 100 | 85 | 75 |
| days 14 | — | 92 | 92 | 87 | 45 |
| days 21 | — | — | 86 | 77 | — |
| months | | | | | |
| 1 | — | 80 | 81 | — | — |
| 2 | — | 77 | — | — | — |
| 2.5 | 96 | 70 | — | — | — |
| 3.5 | — | 77 | — | — | — |
| 4.5 | — | 75 | — | — | — |
| 6 | 96 | 73 | — | — | — |
| 9 | 96 | 65 | — | — | — |
| 12 | 96 | 65 | — | — | — |

STABILITY TEST
LYOPHILE RECONSTITUTED IN WATER
(Retention of antiviral activity)

| Time (weeks) | % of the original antiviral activity | |
|---|---|---|
| | +4° C. | +25° C. |
| 0 | 100 | 100 |
| 1 | 100 | 94 |
| 2 | 98 | 100 |
| 3 | 100 | 89 |
| 4 | 100 | 100 |
| 6 | 100 | 76 |
| 8 | 100 | 52 |
| 10 | 92 | — |
| 12 | 89 | — |
| 14 | 88 | — |
| 16 | 100 | — |
| 18 | 98 | — |
| 20 | 98 | — |
| 22 | 79 | — |
| 24 | 60 | — |

On the basis of the results obtained, it can be seen that the antiviral activity of the lyophile is practically unchanged at +4° C.

If it is kept at a temperature of +25° C. the product retains an antiviral activity within the limits provided for, for two months.

The stability of beta-IFN is also confirmed after exposure to higher temperatures, such as +37° C. for 3 weeks and +45° C. for 1 week.

The lyophilized product appears as a porous, white-coloured mass and, when subjected to testing according to the methods described in official Pharmacopeia Edition VIII by the Ministry of Health, is free of bacteria, fungi, endotoxins and pyrogens.

Moreover, it is very soluble in its diluent and the pH of the solution obtained is approximately 4.5.

The identity of beta-IFN has been confirmed by means of serum neutralization.

We claim:

1. A method for the purification of human interferon from solutions containing it, the method comprising the steps of
   a) providing a column of siliceous material;
   b) disinfecting said column with an aqueous solution of formaldehyde;
   c) passing an interferon solution through said column to substantially completely adsorb said interferon;
   d) washing the column with non-pyrogenic, sterile, deionized water;
   e) eluting of the column successively with a 1.4 M aqueous solution of Nacl in non-pyrogenic, sterile, deionized water, and with an aqueous solution of acetic acid having a molar concentration of from 0.001 M to 0.003 M, to remove residual extraneous proteins;
   f) eluting of the column with an aqueous solution of acetic Acid having a molar concentration of from 0.01 to 0.03 M, to obtain a fraction or fractions of the interferon from the column; and
   g) recovering and lyophilizing the fraction or fractions containing the interferon thus purified.

2. A method according to claim 1, in which the interferon-containing solution is human biological liquid.

3. A method according to claim 1, in which the interferon-containing solution is produced by the culture of human cells.

4. A method according to claim 3, in which the cells are human fibroblasts and the interferon is beta-interferon.

5. A method according to claim 1, in which step c) is carried out at a temperature of about 4° C., and at atmospheric pressure.

6. A method according to claim 1, in which in step c) the adsorbent siliceous material is controlled-porosity glass.

7. A method according to claim 6, in which the controlled-porosity glass material has a mesh size of 120/200, an average pore diameter of 350 Angstrom, a pore spacing of 6.5 ±%, a pore volume of 0.91 cc/g, and surface area of 53.45 m$^2$/g.

8. A method according to claim 1, in which in step b) the disinfection is effected by keeping the column in static contact with a 10% V/V aqueous formaldehyde solution at ambient temperature of 20°-25° C. for 1 night.

9. A method according to claim 1, in which in step e) the molar concentration of the acetic Acid is 0.002 M and the pH of the solution is 3.7.

10. A method according to claim 1, in which in step f) the molar concentration of the acetic Acid is 0.024 and the pH of the solution is 3.2.

11. A method according to claim 1, in which step f) is followed by keeping the column in static contact with an acetic acid solution at a molar concentration of from 0.01 to 0.03 M for a period of from 15 to 30 minutes until the effluent attains an absorbance measured at 280 nm of about 0.05 Arbitrary Full Scale Units, to successively elute the interferon.

12. A method according to claim 1, in which in step g) the lyophilization is effected by placing the purified interferon solution with the addition of excipients and stabilizers, directly on a plate at −42° C. and subsequently bringing the plate to a temperature of +8° C. and keeping it at that temperature from 9 hours;

increasing the temperature of the plate at a constant gradient from +8° C. to +26° C. in 15 hours and keeping the plate at +26° C. for 24 hours and finally keeping the temperature of the plate at +28° C. for about 9 hours.

* * * * *